United States Patent [19]

Beck et al.

[11] Patent Number: 5,406,015

[45] Date of Patent: * Apr. 11, 1995

[54] SELECTIVE ETHYLBENZENE DISPROPORTIONATION PROCESSES (SEBDP) WITH EX SITU SELECTIVATED ZEOLITE CATALYST

[75] Inventors: Jeffrey S. Beck, Princeton, N.J.; Sharon B. McCullen, Newtown, Pa.; David H. Olson, Pennington, N.J.; Chaya R. Venkat, Princeton, N.J.

[73] Assignee: Mobil Oil Corp., Fairfax, Va.

[*] Notice: The portion of the term of this patent subsequent to Nov. 15, 2011 has been disclaimed.

[21] Appl. No.: 69,260

[22] Filed: May 28, 1993

[51] Int. Cl.$^6$ .................................. C07C 5/52
[52] U.S. Cl. ............................ 585/475; 585/470
[58] Field of Search .......................... 585/470, 475

[56] References Cited

U.S. PATENT DOCUMENTS

| | | | |
|---|---|---|---|
| 3,257,310 | 6/1966 | Plank et al. | 208/120 |
| 3,437,587 | 4/1969 | Elbert et al. | 208/120 |
| 3,682,996 | 8/1972 | Kerr | 260/448.8 R |
| 3,698,157 | 10/1972 | Allen et al. | 260/674 |
| 4,016,218 | 4/1977 | Haag et al. | 260/671 R |
| 4,060,568 | 11/1977 | Rodewald | 260/682 |
| 4,086,287 | 4/1978 | Kaeding et al. | 260/671 R |
| 4,090,981 | 5/1978 | Rodewald | 252/455 Z |
| 4,100,215 | 7/1978 | Chen | 260/671 M |
| 4,117,024 | 9/1978 | Kaeding | 260/671 R |
| 4,127,616 | 11/1978 | Rodewald | 260/671 R |
| 4,145,315 | 3/1979 | Rodewald | 252/455 Z |
| 4,224,141 | 9/1980 | Morrison et al. | 208/134 |
| 4,283,306 | 8/1981 | Herkes | 252/432 |
| 4,326,994 | 4/1982 | Haag et al. | 252/455 Z |
| 4,402,867 | 9/1983 | Rodewald | 252/455 |
| 4,443,554 | 4/1984 | Dessau | 502/71 |
| 4,465,886 | 8/1984 | Rodewald | 585/467 |
| 4,477,583 | 10/1984 | Rodewald | 502/71 |
| 4,487,843 | 12/1984 | Telford et al. | 502/85 |
| 4,522,929 | 6/1985 | Chester et al. | 502/77 |
| 4,548,914 | 10/1985 | Chu | 502/85 |
| 4,559,314 | 12/1985 | Shihabi | 502/71 |
| 4,843,057 | 6/1989 | D'Amore et al. | 502/263 |
| 4,851,604 | 7/1989 | Absil et al. | 585/475 |
| 4,927,979 | 5/1990 | Yamagishi et al. | 568/791 |
| 4,950,835 | 8/1990 | Wang et al. | 585/467 |
| 5,173,461 | 12/1992 | Absil et al. | 502/62 |
| 5,243,117 | 9/1993 | Chang et al. | 585/467 |
| 5,248,841 | 9/1993 | Young | 585/475 |

FOREIGN PATENT DOCUMENTS

0296582A2 6/1988 European Pat. Off. .

OTHER PUBLICATIONS

Nakajima et al., "p-Xylene-Selective Disproportionation of Toluene over a Modified Pentasil Type Zeolite", *Sekiyu Gakkaishi*, 35(2), 185–189 (1992).

Hibino et al., "Shape-Selectivity over HZSM-5 Modified by Chemical Vapor Deposition of Silicon Alkoxide", *Journal of Catalysis*, 128, 551–558 (1991).

*Primary Examiner*—Anthony McFarlane
*Attorney, Agent, or Firm*—Alexander J. McKillop; Dennis P. Santini; Edward F. Kenehan, Jr.

[57] ABSTRACT

A process for shape selective hydrocarbon conversion that involves contacting a hydrocarbon feedsteam, including ethylbenzene, under conversion conditions with a catalytic molecular sieve which has been modified by being ex situ selectivated with a silicon compound. The ex situ selectivation involves exposing the molecular sieve to at least two silicon impregnation sequences, each sequence comprising an impregnation with a silicon compound followed by calcination. The modified catalyst used in the process may also be steamed. Optionally, the modified catalyst may be trim-selectivated.

34 Claims, No Drawings

SELECTIVE ETHYLBENZENE DISPROPORTIONATION PROCESSES (SEBDP) WITH EX SITU SELECTIVATED ZEOLITE CATALYST

BACKGROUND OF THE INVENTION

The present invention is directed to shape selective hydrocarbon conversion process over a modified catalytic molecular sieve. The invention also relates to a modified catalytic molecular sieve and a method for its modification.

The term "shape-selective catalysis" describes unexpected catalytic selectivities in zeolites. The principles behind shape selective catalysis have been reviewed extensively, e.g., by N. Y. Chen, W. E. Garwood and F. G. Dwyer, "Shape Selective Catalysis in Industrial Applications," 36, Marcel Dekker, Inc. (1989). Within a zeolite pore, hydrocarbon conversion reactions such as isomerization, disproportionation, alkylation and transalkylation of aromatics are governed by constraints imposed by the channel size. Reactant selectivity occurs when a fraction of the feedstock is too large to enter the zeolite pores to react; while product selectivity occurs when some of the products cannot leave the zeolite channels. Product distributions can also be altered by transition state selectivity in which certain reactions cannot occur because the reaction transition state is too large to form within the zeolite pores or cages. Another type of selectivity results from configurational constraints on diffusion where the dimensions of the molecule approach that of the zeolite pore system. A small change in the dimensions of the molecule or the zeolite pore can result in large diffusion changes leading to different product distributions. This type of shape selective catalysis is demonstrated, for example, in selective ethylbenzene disproportionation to p-diethylbenzene.

The production of para-dialkylbenzene is typically performed by alkylation of alkylbenzene or by alkylbenzene disproportionation over a catalyst under conversion conditions. Such reactions are typified by the reaction of toluene with methanol as described by Chen et al., J. Amer. Chem. Sec. 101, 6783 (1979), and toluene disproportionation, as described by Pines in "The Chemistry of Catalytic Hydrocarbon Conversions", Academic Press, N.Y., 1981, p. 72. These methods typically result in the production of a mixture including para-dialkylbenzene, ortho-dialkylbenzene, and meta-dialkylbenzene. Depending upon the degree of selectivity of the catalyst for para-dialkylbenzene (para-selectivity) and the reaction conditions, different percentages of para-dialkylbenzene are obtained. The yield, i.e., the amount of dialkylbenzene produced as a proportion of the feedstock, is also affected by the catalyst and the reaction conditions.

The equilibrium reaction for the conversion of alkylbenzene to dialkylbenzene and benzene is illustrated by the conversion of toluene to xylene and benzene:

2 Moles Toluene = 184.27 g

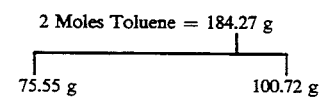

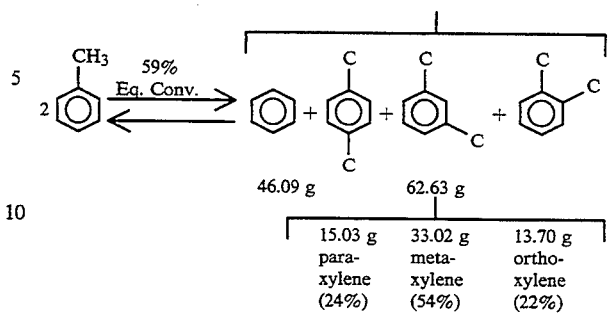

$$\text{p-Xylene Yield} = 100 \times \frac{15.03}{184.27} = 8.2\%$$

$$\text{p-Xylene Selectivity} = 100 \times \frac{15.03}{62.63} = 24\%$$

Various methods are known in the art for increasing the para-selectivity of zeolite catalysts. One such method is to modify the catalyst by treatment with a "selectivating agent". For example, U.S. Pat. Nos. 5,173,461, 4,950,835, 4,927,979, 4,465,886, 4,477,583, 4,379,761, 4,145,315, 4,127,616, 4,100,215, 4,090,981, 4,060,568 and 3,698,157 disclose specific methods for contacting a catalyst with a selectivating agent containing silicon ("silicon compound").

U.S. Pat. No. 4,548,914 describes another modification method involving impregnating catalysts with oxides that are difficult to reduce, such as those of magnesium, calcium, and/or phosphorus, followed by treatment with water vapor to improve para-selectivity.

European Patent No. 296,582 describes the modification of aluminosilicate catalysts by impregnating such catalysts with phosphorus-containing compounds and further modifying these catalysts by incorporating metals such as manganese, cobalt, silicon and Group IIA elements. The patent also describes the modification of zeolites with silicon compounds.

Traditionally, ex situ selectivation of zeolites has involved single applications of the selectivating agent. It may be noted, however, that the suggestion of multiple treatments was made in U.S. Pat. No. 4,283,306 to Herkes. The Herkes patent discloses the promotion of crystalline silica catalyst by application of an amorphous silica such as ethylorthosilicate. The Herkes patent contrasts the performance of catalyst treated once with an ethylorthosilicate solution followed by calcination against the performance of catalyst treated twice with ethylorthosilicate and calcined after each treatment. The Herkes disclosure shows that the twice-treated catalyst is less active and less selective than the once-treated catalyst as measured by methylation of toluene by methanol, indicating that multiple ex situ selectivation confers no benefit and in fact reduces a catalyst's efficacy in shape-selective reactions.

There has been no suggestion, however, that the selectivation of zeolites by the multiple ex situ impregnation of the zeolites with selectivating agents such as silicon compounds, followed by calcination after each impregnation would improve the selectivity and activity of the catalysts. It has now been found that a multiple impregnation scheme provides unexpectedly better results in shape-critical ethylbenzene conversions than single silicon impregnation pre-treatment schemes.

It has also now been found that a multiple impregnation scheme provides unexpectedly more efficient deposition of the selectivating agent on the catalyst than schemes employing impregnations.

Steaming has also been used in the preparation of zeolite catalysts to modify the alpha or improve stability. For example, U.S. Pat. No. 4,559,314 describes steaming a zeolite/binder composite at 200°–500° C. for at least an hour to enhance activity by raising the alpha. U.S. Pat. No. 4,522,929 describes pre-steaming a fresh zeolite catalyst so that the alpha activity first rises then falls to the level of the fresh unsteamed catalyst, producing a stable catalyst which may be used in xylene isomerization. U.S. Pat. No. 4,443,554 describes steaming inactive zeolites (Na ZSM-5) to increase alpha activity. U.S. Pat. No. 4,487,843 describes contacting a zeolite with steam prior to loading with a Group IIIB metal.

It has also now been found that a multiple impregnation scheme for zeolite catalyst selectivation followed by steam treatment produces additional unexpectedly better results than the multiple impregnation treatment alone. It has also been found that the optional steam treatment, to be advantageous according to the present invention, must be performed within a limited range of conditions.

Accordingly, it is an object of the invention to improve selectivity in catalytic molecular sieves thereby improving shape selectivity in hydrocarbon conversion processes over the molecular sieves.

Various organic compounds have been employed as carriers for selectivating agents in the impregnation methods applied to zeolite catalysts. For example, U.S. Pat. Nos. 4,145,315, 4,127,616, 4,090,981 and 4,060,568 describe the use of inter alia $C_{5-7}$ alkanes as solvents for impregnation of zeolites with selectivating agents containing silicon.

There has been no suggestion, however, of the use of lower volatility alkanes as carriers for impregnation of zeolites. It has now been found that organic carriers of lower volatility and flammability, having the advantages of ease and safety of industrial application, unexpectedly provide results that are at least substantially equivalent to those achieved by employment of solvents having higher volatility.

Accordingly, it is another object of the invention to provide for the use of organic carriers of lower volatility and flammability and thereby to improve the ease with which silicon impregnation of zeolite catalysts may be achieved as well as to improve the safety of such method.

SUMMARY OF THE INVENTION

The invention is a process of shape selective ethylbenzene disproportionation over a modified catalytic molecular sieve by contacting a reaction stream comprising ethylbenzene, under conversion conditions, with a modified catalytic molecular sieve. The modification method includes exposing the catalytic molecular sieve to at least two ex situ selectivation sequences. Each ex situ selectivation sequence includes impregnating the catalytic molecular sieve with a selectivating agent, followed by calcination after each impregnation. Selectivating agents useful in the present invention include a large variety of silicon-containing compounds, preferably silicon polymers soluble in organic carriers. Such organic carriers include various alkanes, preferably paraffins having 7 or more carbons.

The invention further includes a process of shape selective disproportionation of ethylbenzene by contacting a reaction stream comprising ethylbenzene, under conversion conditions, with a modified catalytic molecular sieve that has been further modified by steaming the modified catalytic molecular sieve at moderate temperatures.

The invention also includes a process of shape selective ethylbenzene disproportionation over a modified catalytic molecular sieve that has been optionally further modified by steaming at moderate temperatures and that has been further modified by in situ trim-selectivating the modified catalytic molecular sieve. The in situ trim-selectivating may be performed by coke trim-selectivating wherein an organic compound is decomposed in the presence of the modified catalytic molecular sieve, at conditions suitable for decomposing the organic compound. Alternatively, the trim-selectivating may be performed by exposing the modified catalytic molecular sieve to a reaction stream that includes a hydrocarbon to be converted and a trim-selectivating agent selected from a group of compounds including a large variety of silicon-containing compounds, at reaction conditions.

Advantageously, the described modified catalysts have enhanced shape selectivity for para-xylene production. Accordingly, the disproportionation process of the invention exhibits increased selectivity for para-xylene and may exhibit an increased ethylbenzene disproportionation rate constant.

DETAILED DESCRIPTION OF THE INVENTION

The present invention relates to enhanced shape selective production of dialkyl-substituted benzenes, including the shape selective disproportionation of ethylbenzene to commercially useful para-diethylbenzene.

The catalytic molecular sieves useful herein have a Constraint Index from about 1 to about 12 and include intermediate pore zeolites. Zeolites which conform to the specified values of constraint index for intermediate pore zeolites include ZSM-5, ZSM-11, ZSM-5/ZSM-11 intermediate, ZSM-12, ZSM-22, ZSM-23, ZSM-35, ZSM-48, ZSM-50, and ZSM-57. Such zeolites are described, for example, in U.S. Pat. Nos. 3,702,886 and Re. No. 29,949, 3,709,979, 3,832,449, 4,046,859, 4,556,447, 4,076,842, 4,016,245, 4,229,424, 4,397,827, 4,640,849, 4,046,685, 3,308,069 and Re. 28,341, to which reference is made for the details of these zeolites.

For the process of the present invention, a zeolite, either incorporated with a binder or in unbound form, is impregnated at least twice, preferably between about two and about six times, with a selectivating agent. The selectivating agent comprises a compound or polymer containing a main group or transition metal, preferably silicon. In each phase of the selectivation treatment, the selectivating agent is deposited on the external surface of the catalyst by any suitable method. For example, the silicon compound may be dissolved in a carrier, mixed with the catalyst, and then dried by evaporation or vacuum distillation. This method is termed "impregnation". The molecular sieve may be contacted with the silicon compound at a molecular sieve/silicon compound weight ratio of from about 100/1 to about 1/100.

The silicon compound employed may be in the form of a solution, an emulsion, a liquid or a gas under the conditions of contact with a zeolite. The deposited silicon compound extensively covers, and resides substantially exclusively on, the external surface of the molecular sieve. Examples of methods of depositing silicon on the surface of the zeolite are found in U.S. Pat. Nos. 4,090,981, 4,127,616, 4,465,886 and 4,477,583 to Rodewald, which are incorporated by reference herein. Further examples of the deposition of a silicon compound on zeolite surfaces are described in H. Nakajima, M. Koya, H. Ishida, and M. Kohno, Sekiyu Gakkaishi, 35(2) (1992), and in U.S. Pat. No. 4,950,835 to Wang et al.

As was described above, the catalysts useful in the present invention are ex situ selectivated by multiple coatings with a high efficiency, para-selectivating agent, each coating followed by calcination and optional trim-selectivated with additional high efficiency para-selectivating agent. As used herein, the term "high efficiency, para-selectivating agent" is used to indicate substances which will increase the para-selectivity of a catalytic molecular sieve to the stated levels in ethylbenzene disproportionation while maintaining commercially acceptable levels of ethylbenzene to diethylbenzene conversion. Such substances include, for example, organic silicon compounds such as phenylmethyl silicone, dimethyl silicone, and blends thereof which have been found to be suitable. For trim-selectivation these agents may also include organic compounds such as toluene and ethylbenzene.

Useful selectivating agents include siloxanes which can be characterized by the general formula:

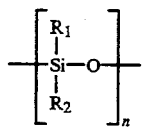

where $R_1$ is hydrogen, halogen, hydroxyl, alkyl, halogenated alkyl, aryl, halogenated aryl, aralkyl, halogenated aralkyl, alkaryl or halogenated alkaryl. The hydrocarbon substituents generally contain from 1 to 10 carbon atoms, preferably methyl or ethyl groups. $R_2$ is independently selected from the same group as $R_1$, and n is an integer of at least 2 and generally in the range of 3 to 1000. The molecular weight of the silicone compound employed is generally between about 80 and about 20,000 and preferably within the approximate range of 150 to 10,000. Representative silicone compounds include dimethyl silicone, diethyl silicone, phenylmethyl silicone, methylhydrogen silicone, ethylhydrogen silicone, phenylhydrogen silicone, methylethyl silicone, phenylethyl silicone, diphenyl silicone, methyltrifluoropropyl silicone, ethyltrifluoropropyl silicone, polydimethyl silicone, tetrachlorophenylmethyl silicone, tetrachlorophenylethyl silicone, tetrachlorophenylhydrogen silicone, tetrachlorophenylphenyl silicone, methylvinyl silicone and ethylvinyl silicone. The silicone compound need not be linear, but may be cyclic, for example, hexamethyl cyclotrisiloxane, octamethyl cyclotetrasiloxane, hexaphenyl cyclotrisiloxane and octaphenyl cyclotetrasiloxane. Mixtures of these compounds may also be used, as may silicones with other functional groups.

Other silicon compounds, including silanes and alkoxy silanes, such as tetramethoxy silane, may also be utilized. These useful silicon-containing selectivating agents include silanes characterizable by the general formula:

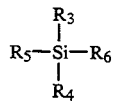

where $R_1$, $R_2$, $R_3$ and $R_4$ are independently selected from the group consisting of hydrogen, hydroxyl, halogen, alkyl, halogenated alkyl, alkoxy, aryl, halogenated aryl, aralkyl, halogenated aralkyl, alkaryl, and halogenated alkaryl groups. Mixtures of these compounds may also be used.

Preferred silicon-containing selectivating agents include dimethylphenylmethyl polysiloxane (e.g., Dow-550) and phenylmethyl polysiloxane (e.g., Dow-710). Dow-550 and Dow-710 are available from Dow Chemical Co., Midland, Mich.

Preferably, the kinetic diameter of the high efficiency, p-diethylbenzene selectivating agent is larger than the zeolite pore diameter, in order to avoid entry of the selectivating agent into the pore and any concomitant reduction in the internal activity of the catalyst.

Examples of suitable carriers for the selectivating silicon compound include linear, branched, and cyclic alkanes having five or more carbons. In the methods of the present invention it is preferred that the carrier be a linear, branched, or cyclic alkane having a boiling point greater than about 70° C., and most preferably containing 7 or more carbons. Optionally, mixtures of low volatility organic compounds, such as hydrocracker recycle oil, may be employed as carriers. The most preferred low volatility hydrocarbon carriers are decane and dodecane.

It has been found that a multiple selectivation scheme provides unexpectedly increased efficiency of deposition of the silicon compound on the surface of the catalyst. This increased efficiency allows for the use of relatively small quantities of the silicon compound as well as relatively small quantities of the carrier.

Following each deposition of the silicon compound, the catalyst is calcined to decompose the molecular or polymeric species to a solid state species. The catalyst may be calcined at a rate of from about 0.2° C./minute to about 5° C./minute to a temperature greater than 200° C., but below a temperature at which the crystallinity of the zeolite is adversely affected. Generally, such temperature will be below 600° C. Preferably the temperature of calcination is within the approximate range of 350° C. to 550° C. The product is maintained at the calcination temperature usually for 1 to 24 hours, preferably for between 2 and 6 hours.

The catalyst may be calcined in an atmosphere of $N_2$, an oxygen-containing atmosphere, preferably air, an atmosphere of $N_2$ followed by an oxygen-containing atmosphere, or an atmosphere containing a mixture of $N_2$ and air. Calcination should be performed in an atmosphere substantially free of water vapor, to avoid undesirable uncontrolled steaming of the silicon coated catalyst. The catalyst may be calcined once or more than once after each silicon deposition. The various calcinations in any impregnation sequence need not be identical, but may vary with respect to the temperature, the rate of temperature rise, the atmosphere and the duration of calcination.

Factors upon which the amount of silica incorporated with the zeolite is dependent include temperature, concentration of the silicon compound in the containing medium, the degree to which the zeolite has been dried prior to contact with the silicon compound, and calcination of the zeolite.

After the selectivation sequence, the catalyst may be subjected to steam treatment at a temperature of from about 100° C. to about 600° C., preferably from about 175° C. to about 325° C.; with from about 1% to about 100% steam, preferably from about 50% to about 100% steam; at a pressure of from about 0.01 psia to about 50 psia; for about two to about twelve hours, preferably from about three to about six hours.

The selectivated molecular sieve catalyst, with or without binder, can show improved selectivity upon steaming. Alternatively, excessive steaming can be detrimental to a selectivated catalyst.

The alkylbenzene may be fed simultaneously with a second selectivating agent and hydrogen at reaction conditions until the desired p-dialkylbenzene selectivity, e.g., 90%, is attained, whereupon the co-feed of selectivating agent is discontinued. This co-feeding of selectivating agent with alkylbenzene is termed "trim-selectivation". Reaction conditions for this in situ trim-selectivation step generally include a temperature of from about 350° C. to about 650° C. and a pressure of from about atmospheric to about 5000 psig. The reaction stream is fed to the system at a rate of from about 0.1 WHSV to about 20 WHSV. Hydrogen may be fed at a hydrogen to hydrocarbon molar ratio of from about 0.1 to about 20. Typically, coke trimming is conducted at conditions outside the operating parameters used during the main time span of the catalytic cycle.

The high efficiency para-dialkylbenzene selectivating agent for trim-selectivation may comprise a silicon compound discussed in greater detail above. For example, organic silicon compounds such as phenylmethyl silicone, dimethyl silicone, and mixtures thereof are suitable. According to one embodiment of the present invention, a silicone containing phenylmethylsilicone and dimethylsilicone groups in a ratio of about 1:1 is co-fed to the system, while the other components, e.g., alkylbenzene and hydrogen, are fed in the amounts set forth above. The high-efficiency para-dialkylbenzene selectivating agent is fed in an amount of from about 0.001 wt. % to about 10 wt. % of the alkylbenzene according to this preferred embodiment. Depending upon the percentage of selectivating agent used, the trim-selectivation will last for at least one hour, preferably about 1 to about 48 hours, most preferably less than 24 hrs.

In this scheme the silicon compound will decompose to deposit additional silica to on the catalyst. During the selectivation procedure the para-selectivity of the catalyst will be observed to increase further. The silicon containing polymer or molecular species may be dissolved in toluene or other appropriate aromatic or hydrocarbon carrier.

Alternatively, the catalyst, prior to contacting with alkylbenzene under disproportionation conditions, may be subjected to trim-selectivation with a thermally decomposable organic compound at an elevated temperature in excess of the decomposition temperature of said compound but below the temperature at which crystallinity of the zeolite is adversely affected. Generally, this temperature will be less than about 650° C.

Organic materials, thermally decomposable under the above temperature conditions to provide coke trimming, encompass a wide variety of compounds including by way of example, hydrocarbons, such as paraffinic, cycloparaffinic, olefinic, cycloolefinic and aromatic; oxygen-containing organic compounds such as alcohols, aldehydes, ethers, ketones and phenols; heterocyclics such as furans, thiophenes, pyrroles and pyridines. Usually, it is contemplated that a thermally decomposable hydrocarbon, such as an alkyl-substituted aromatic, will be the source of coke, most preferably the alkylbenzene being subjected to disproportionation itself. In the latter case, the alkylbenzene is initially brought into contact with the catalyst under conditions of temperature and hydrogen concentration amenable to rapid coke formation. Typically, coke trimming is conducted at conditions outside the operating parameters used during the main time span of the catalytic cycle. When the desired coke deposition has been effected, the alkyl-benzene feed is continued in contact with the coke-containing catalyst under conditions of temperature and hydrogen concentration conducive to disproportionation, with a greatly reduced coking rate.

While not wishing to be bound by theory, it is believed that the advantages of the present invention are in part obtained by rendering acid sites on the external surfaces of the catalyst substantially inaccessible to reactants, while increasing catalyst tortuosity. Acid sites existing on the external surface of the catalyst are believed to isomerize the solution-phase p-dialkylbenzene back to an equilibrium level with the other two dialkylbenzene isomers, in the case of xylenes thereby reducing the amount of p-xylene in the xylenes to only about 24%. By reducing the availability of these acid sites to the solution-phase p-dialkylbenzene, the relatively high proportion of p-dialkylbenzene can be maintained. It is believed that the high-efficiency, p-dialkylbenzene selectivating agents of the present invention block or otherwise render these external acid sites unavailable to the p-dialkylbenzene by chemically modifying said sites.

Disproportionation of Alkyl-Substituted Benzenes

The modified zeolite catalysts useful in the present invention are advantageously used in the conversion of aromatics compounds to provide dialkyl-substituted benzene products which are highly enriched in the para-dialkyl substituted benzene isomer. Conversion reactions of this type include alkylation, transalkylation and disproportionation of aromatics. Alkylations of aromatics in which the catalysts of the invention can be used are described, for example, in U.S. Pat. Nos. 3,755,483, 4,086,287, 4,117,024 and 4,117,026, which are incorporated herein by reference.

As described in U.S. Pat. No. 3,755,483 to Burress, aromatic hydrocarbons such as benzenes, naphthalenes, anthracenes and substituted derivatives thereof, e.g., toluene and xylene, may be alkylated with alkylating agents such as olefins ethylene, propylene, dodecylene, and formaldehyde, alkyl halides, and alkyl alcohols with 1 to 24 carbons under vapor phase conditions including a reactor inlet temperature up to about 482° C., with a reactor bed temperature up to about 566° C., at a pressure of about atmospheric to about 3000 psia, a mole ratio of aromatic/alkylating agent of from about 1:1 to about 20:1, and a WHSV of 20 to 3000 over ZSM-12 which is a ZSM-5 type catalyst.

As described in U.S. Pat. No. 4,086,287 to Kaeding et al., monoalkylbenzenes having alkyls of 1-2 carbons, such as toluene and ethylbenzene, may be ethylated to produce a para-ethyl derivative, e.g., para-ethyltoluene at a temperature of from about 250° C. to about 600° C., a pressure of 0.1 atmospheres to 100 atmospheres, a weight hourly space velocity (WHSV) of 0.1 to 100, and a ratio of feed/ethylating agent of 1 to 10 over a catalyst having an acid activity, i.e., alpha, of 2 to 5000, modified by pre-coking or combining with oxides of phosphorus, boron or antimony to attain a catalyst with a xylene sorption capacity greater than 1 g/100 g of zeolite and an ortho-xylene sorption time for 30% of said capacity of greater than 10 minutes, where sorption capacity and sorption time are measured at 120° C. and a xylene pressure of 4.5±0.8 mm of mercury.

U.S. Pat. No. 4,117,024 to Kaeding describes a process for the ethylation of toluene or ethylbenzene to produce p-ethyltoluene at a temperature of 350° C. to 550° C., a critical pressure of greater than one atmosphere and less than 400 psia, with hydrogen/ethylene ratio of 0.5 to 10 to reduce aging of the catalyst. The zeolite described in U.S. Pat. No. 4,117,024 has a crystal size greater than one micron, and is modified as the catalyst in U.S. Pat. No. 4,086,287 to attain the sorption capacity described in U.S. Pat. No. 4,086,287.

U.S. Pat. No. 4,117,026 to Haag and Olson describes the production of para-dialkyl benzenes having alkyls of 1 to 4 carbons under conditions which vary according to the feed. When the feed includes monoalkyl-substituted benzenes having an alkyl group of 1 to 4 carbons, olefins of 2 to 15 carbons, or paraffins of 3 to 60 carbons or mixtures thereof, conversion conditions include a temperature of 250° C. to 750°, a pressure of 0.1 to 100 atmospheres and a WHSV of 0.1 to 2000. For the disproportionation of toluene, the conditions include a temperature of 400° C. to 700° C., a pressure of 1 to 100 atmospheres and a WHSV of 1-50. When the feed includes olefins of 2 to 15 carbons including cyclic olefins, the conversion conditions include a temperature of 300° C. to 700° C., a pressure of 1 to 100 atmospheres and a WHSV of 1 to 1000. When the feed includes paraffins of 3 to 60 carbons, conditions include a temperature of 300° C. to 700° C., a pressure of 1 to 100 atmospheres and a WHSV of 0.1 to 100. However for lower paraffins of 3 to 5 carbons, the temperature should be above 400° C. When the feed includes mixed aromatics such as toluene and ethylbenzene, and also optionally olefins of 2 to 20 carbons or paraffins of 5 to 25 carbons, conversion conditions include a temperature of 250° C. to 500° C. and a pressure greater than 200 psia. In the absence of added aromatics, the olefins and higher paraffins are more reactive and require lower severity of operation, e.g., a temperature of 250° C. to 600° C., preferably 300° C. to 550° C.

In general, therefore, catalytic conversion conditions over a catalyst comprising the modified zeolite include a temperature of from about 100° C. to about 760° C., a pressure of from about 0.1 atmosphere (bar) to about 200 atmospheres (bar), a weight hourly space velocity of from about 0.08 to about 2000, and a hydrogen/organic, e.g., hydrocarbon compound, mole ratio of from 0 to about 100.

Ethylbenzene Disproportionation

The present invention generally involves the shape selective disproportionation of alkyl-substituted benzenes, namely ethylbenzene, over a multiply-selectivated and optionally steamed catalyst. Normally a single pass conversion of an ethylbenzene stream results in a product stream which includes diethylbenzenes having alkyl groups at all locations, i.e., o-, m-, and p-diethylbenzenes. A catalyst treated in the manner described herein exhibits a desirable decreased o-diethylbenzene sorption rate parameter and yields a significantly para-selected product from ethylbenzene disproportionation. For example, diffusion rate constants in toluene disproportionation have been discussed by D. H. Olson and W. O. Haag, "Structure-Selectivity Relationship in Xylene Isomerization and Selective Toluene Disproportionation", *Catalytic Materials: Relationship Between Structure and Reactivity*, ACS Symposium Ser. No. 248 (1984).

In toluene disproportionation, toluene diffuses into the zeolite with a diffusivity $D_T$. The toluene undergoes disproportionation to p-, m-, and o-xylene and benzene at a total rate constant $k_D$. For high selectivity and catalyst efficiency it is desirable to have:

$$k_D << \frac{D_T}{r^2}.$$

The degree of para-selectivity depends on the activity and the diffusion characteristics of the catalyst. The primary product will be rich in the para isomer if initially produced m- and o-xylene diffuse out of the zeolite crystal at a rate $(D_{m,o}/r^2)$ that is lower than that of their conversion to p-xylene $(k_I)$, as well as lower than that of the p-xylene diffusion $(D_p/r^2)$ out of the catalyst, where:

$D_m$=diffusion of m-xylene;
$D_o$=diffusion of o-xylene;
$D_p$=diffusion of p-xylene;
r=length of diffusion path (crystal size);
$k_I$=rate of interconversion via isomerization of xylene isomers yielding secondary xylene product m-xylene and o-xylene.

It is desirable to increase the para-selectivity of the catalyst. Practically, this involves decreasing the o- and m-xylene diffusivities such that $$k_1 > \frac{D_{m,o}}{r^2}.$$

In such a case the rate of conversion of m- and o-xylenes to p-xylene exceeds the diffusivities of the m- and o-xylenes. As a result, the proportion of the xylene yield that is p-xylene will be increased. Those skilled in the art will appreciate that similar considerations apply to the diffusivities of other alkylbenzenes.

The invention also comprises the near regioselective conversion of ethylbenzene to para-diethylbenzene by disproportionating ethylbenzene in a reaction stream containing a ethylbenzene feed with a selectivated and optionally steamed catalytic molecular sieve in the presence of hydrogen and at reaction conditions suitable to provide p-diethylbenzene selectivity of greater than about 80%, preferably greater than 90%. The production stream may also contain small amounts of o- and m-diethylbenzene and trace amounts of impurities.

As used herein, the term "para-diethylbenzene selectivity" means the proportion of p-diethylbenzene, indicated as a percentage, among all of the diethylbenzene products, i.e., p-diethylbenzene, o-diethylbenzene, and m-diethylbenzene. Those skilled in the art will appreciate that the relative proximity of the boiling points of these diethylbenzene isomers necessitates relatively expensive separation processes for the isolation of p-diethylbenzene. On the other hand, p-diethylbenzene is more readily separated from other components in the product stream such as benzene, ethylbenzene, and p-ethylethylbenzene.

Furthermore, the dialkylbenzenes are known to proceed in reactions which produce unwanted heavier alkylbenzenes. For example, the xylenes can react to produce unwanted ethylbenzenes by the following reaction:

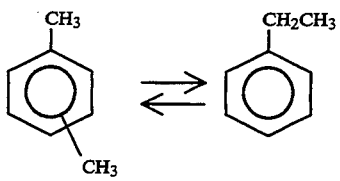

As explained in greater detail herein, the present invention provides a process for obtaining p-diethylbenzene at ethylbenzene conversions of at least 10%, preferably at least about 15–25%, with a p-diethylbenzene selectivity of greater than 85%, preferably at least 95%.

The ethylbenzene feedstock preferably includes about 50% to 100% ethylbenzene, more preferably at least about 80% ethylbenzene. Other compounds such as benzene, diethylbenzenes, and triethylbenzenes may also be present in the ethylbenzene feedstock without adversely affecting the present invention.

The ethylbenzene feedstock may also be dried, if desired, in a manner which will minimize moisture entering the reaction zone. Numerous methods known in the art are suitable for drying the ethylbenzene charge for the process of the invention. These methods include percolation through any suitable desiccant, for example, silica gel, activated alumina, molecular sieves or other suitable substances, or the use of liquid charge dryers.

The catalytic molecular sieves useful in accordance with the methods of the present invention are preferably in the hydrogen form prior to modification, but may be in the ammonium or sodium form. Preferably, the catalytic molecular sieve comprises an intermediate pore-size zeolite such as a ZSM-5, ZSM-11, ZSM-22, ZSM-23, or ZSM-35 as discussed above. The catalytic molecular sieves also preferably have a Constraint Index of about 1–12. The details of the method by which Constraint Index is determined are described fully in U.S. Pat. No. 4,016,218, incorporated herein by reference.

The crystal size of zeolites used herein is preferably greater than 0.1 micron. The accurate measurement of crystal size of zeolite materials is frequently very difficult. Microscopy methods, such SEM and TEM, are often used, but these methods require measurements on a large number of crystals and for each crystal measured, values may be required in up to three dimensions. For ZSM-5 materials described in the examples below, estimates were made of the effective average crystal size by measuring the rate of sorption of 2,2-dimethylbutane at 90° C. and 60 torr hydrocarbon pressure. The crystal size is computed by applying the diffusion equation given by J. Crank, "The Mathematics of Diffusion", Oxford at the Clarendon Press, 1957, pp 52–56, for the rate of sorbate uptake by a solid whose diffusion properties can be approximated by a plane sheet model. In addition, the diffusion constant of 2,2-dimethylbutane, D, under these conditions is taken to be $1.5 \times 10^{-14}$ cm$^2$/sec. The relation between crystal size measured in microns, d, and diffusion time measured in minutes, $t_{0.3}$, the time required for the uptake of 30% of capacity of hydrocarbon, is:

$$d = 0.0704 \times t_{0.3}^{\frac{1}{2}}.$$

In the present case these measurements have been made on a computer controlled, thermogravimetric electrobalance, but there are numerous ways one skilled in the art could obtain the data. The larger crystal material used herein has a sorption time, $t_{0.3}$, of 497 minutes, which gives a calculated crystal size of 1.6 microns. The smaller crystal material has a sorption time of 7.8 minutes, and a calculated crystal size of 0.20 micron.

The "alpha value" of a catalyst is an approximate indication of the catalytic cracking activity of the catalyst compared to a standard catalyst, and it gives the relative rate constant (rate of normal hexane conversion per volume of catalyst per unit time). It is based on the activity of the amorphous silica-alumina cracking catalyst taken as an alpha of 1 (Rate Constant=0.016 sec$^{-1}$). The alpha test is described in U.S. Pat. No. 3,354,078 and in *The Journal of Catalysis*, Vol. 4, pp. 522–529 (August 1965); Vol. 6, p. 278 (1966); and Vol. 61, p. 395 (1980), each incorporated herein by reference as to that description. It is noted that intrinsic rate constants for many acid-catalyzed reactions are proportional to the alpha value for a particular crystalline silicate catalyst (see "The Active Site of Acidic Aluminosilicate Catalysts," *Nature*, Vol. 309, No. 5959, pp. 589–591, 14 Jun. 1984). The experimental conditions of the test used herein include a constant temperature of 538° C. and a variable flow rate as described in detail in the *Journal of Catalysis*, Vol. 61, p. 395 (1980). The catalyst in the present invention preferably has an alpha value greater than 1, for example, from about 1 to about 2000. The alpha value of the catalyst may be increased by initially treating the catalyst with nitric acid or by mild steaming before pre-selectivation. This type of steaming is discussed in U.S. Pat. No. 4,326,994.

The silica to alumina ratio of the catalysts of the invention may be determined by conventional analysis. This ratio is meant to represent, as closely as possible, the ratio in the rigid atomic framework of the zeolite crystal and to exclude aluminum in the binder or in cationic or other form within the channels. Although zeolites with a silica to alumina ratio of up to about 10,000 are useful, it is preferred to use zeolites having ratios of at least about 20 to about 2000.

For the improved disproportionation process of this invention, the suitable molecular sieve may be employed in combination with a support or binder material such as, for example, a porous inorganic oxide support or a clay binder. While the preferred binder is silica, other non-acidic binder materials may be employed, generally in the form of dried inorganic oxide gels or gelatinous precipitates. Suitable clay materials include, by way of example, bentonite and kieselguhr. The relative proportion of suitable crystalline molecular sieve to the total composition of catalyst and binder or support may be from about 30% to about 98% by weight and is preferably from about 50% to about 80% by weight of the composition. The composition may be in the form of an extrudate, beads or fluidizable microspheres.

Operating conditions employed in the process of the present invention will affect the para-selectivity and ethylbenzene conversion. Such conditions include the temperature, pressure, space velocity, molar ratio of the reactants, and the hydrogen to hydrocarbon mole ratio (H$_2$/HC). It has also been observed that an increased space velocity (WHSV) can enhance the paraselectivity of the modified catalyst in alkylbenzene disproportionation reactions. This characteristic of the modified catalyst allows for substantially improved throughput when compared to current commercial practices. In addition, it has been observed that the disproportionation process may be performed using $H_2$ as a diluent, thereby dramatically increasing the cycle length of the catalyst. For example, it has been observed that an increase in temperature can increase the activity of the modified catalyst. In addition, it has been observed that the ethylbenzene disproportionation process may be performed using $H_2$ as a diluent, thereby dramatically increasing the cycle length of the catalyst.

A selectivated and steamed catalytic molecular sieve may be contacted with a ethylbenzene feedstock under conditions for effecting vapor-phase disproportionation. Conditions effective for accomplishing the high para-selectivity and acceptable ethylbenzene disproportionation conversion rates include a reactor inlet temperature of from about 200° C. to about 600° C., preferably from 350° C. to about 540° C.; a pressure of from about atmospheric to about 5000 psia, preferably from about 100 to about 1000 psia; a WHSV of from about 0.1 to about 20, preferably from about 2 to about 10; and a $H_2/HC$ mole ratio of from about 0.1 to about 20, preferably from about 2 to about 6. This process may be conducted in either batch or fluid bed operation, with the attendant benefits of either operation readily obtainable. The effluent may be separated and distilled to remove the desired product, i.e., p-diethylbenzene, as well as other by-products. Alternatively, the $C_8$ fraction may be subjected to further separation via crystallization to yield p-diethylbenzene.

The following non-limiting Examples illustrate the invention in relation to the disproportionation of ethylbenzene as well as in the related disproportionation of toluene.

In the Examples, the o-diethylbenzene sorption rate parameter $D_o/r^2$ was measured at 120° C. and 3.8 torr.

$D_o$ = diffusivity of o-diethylbenzene
r = crystal size
$D_o/r^2$ = the diffusion rate parameter which is a measure of the speed of the movement of o-xylene in and out of the catalyst crystal.

Also in the Examples, the atmospheric toluene disproportionation (TDP) test was performed at 482° C., 1 atmosphere, at 4% conversion. The TDP rate constant for the catalyst was obtained under these same conditions.

EXAMPLE 1

The atmospheric TDP test to screen catalyst activity and selectivity was performed as follows using a sample of HZSM-5/SiO$_2$ (65% HZM-5/35% SiO$_2$) with a crystal size of 1.6 microns. The untreated sample was reacted with toluene at atmospheric pressure at 482° C., and the toluene conversion was varied by adjusting the toluene WHSV. The para-selectivity of the untreated catalyst was 37% at 4% toluene conversion, with a TDP rate constant of 167. The o-xylene diffusivity of the untreated catalyst was $4.7 \times 10^{-6}$, and the n-hexane sorption was 69 mg/g.

EXAMPLE 2

To 8.0 grams of the untreated catalyst (Ex. 1) was added 1.55 grams of dimethylphenylmethyl polysiloxane (Dow-550) dissolved in 40 cc of hexane. The catalyst was agitated in the silicone solution for several minutes and the hexane was distilled off by high vacuum distillation. After allowing the dry catalyst to cool to room temperature, the sample was then calcined in air at 1° C./min to 538° C. and held for 3 hours. The silica modified catalyst had gained 3.7 wt. %, presumably as $SiO_2$.

The atmospheric TDP test was performed on the once-treated catalyst, as described in Example 1. The para-selectively of the catalyst was 67.3% at 4% toluene conversion, with a TDP rate constant of 226. The o-xylene diffusivity was decreased to $1.1 \times 10^{-6}$, and the n-hexane sorption was 68 mg/g.

EXAMPLE 3

To 5.75 grams of the once-treated catalyst (Ex. 2) was added 1.12 grams of dimethylphenylmethyl polysiloxane (Dow-550) dissolved in 40 cc of hexane. The catalyst was agitated in the silicone solution for several minutes and the hexane was distilled off by high vacuum distillation. After allowing the dry catalyst to cool to room temperature, the sample was then calcined in air at 1° C./min. to 538° C. and held for 3 hours. The silica modified catalyst had gained an additional 5.0 wt. %, presumably as $SiO_2$.

The atmospheric TDP test was performed on the twice-treated catalyst, as described in Example 1. The para-selectivity of the catalyst was increased to 92.9% at 4% toluene conversion, with a TDP rate constant of 251. The o-xylene diffusivity was lowered to $0.29 \times 10^{-6}$, and the n-hexane sorption was 65 mg/g.

EXAMPLE 4

To 4.18 grams of the twice-treated catalyst (Ex. 3) was added 0.81 grams of dimethylphenylmethyl polysiloxane (Dow-550) dissolved in 40 cc of hexane. The catalyst was agitated in the silicone solution for several minutes and the hexane was distilled off by high vacuum distillation. After allowing the dry catalyst to cool to room temperature, the sample was then calcined in air at 1° C./min. to 538° C. and held for 3 hours. The silica modified catalyst had gained an additional 0.8 wt. %, presumably as $SiO_2$.

The atmospheric TDP test was performed on the twice-treated catalyst, as described in Example 1. The para-selectivity of the catalyst was 99.1% at 4% toluene conversion, with a TDP rate constant of 249. The o-xylene diffusivity was further decreased to $0.073 \times 10^{-6}$, and the n-hexane sorption was 64 mg/g.

A comparison of the characteristics of the untreated catalyst and the three silicone treated catalysts described in Examples 1–4, is provided below in Table 1.

TABLE 1

Characterization of Silicone Treated HZSM-5/SiO$_2$ Catalyst

| Catalyst | Silica Treatment | D/r$^2$ | p-xyl/xyl (%) | K | n-hexane sorption mg/g |
|---|---|---|---|---|---|
| Example 1 (Untreated) | None | $4.7 \times 10^{-6}$ | 37.0 | 167 | 69 |
| Example 2 | 1 | $1.1 \times 10^{-6}$ | 67.3 | 226 | 68 |
| Example 3 | 2 | $0.29 \times 10^{-6}$ | 92.9 | 251 | 65 |
| Example 4 | 3 | $0.073 \times 10^{-6}$ | 99.1 | 249 | 64 |

The results of Examples 1–4 show that multiple silicone coatings applied to a zeolite catalyst significantly change the characteristics of the catalyst. The triply-treated catalyst showed an extremely high para-selectivity of 99.1% compared to 37.0% for the untreated material. It will also be noted that the n-hexane sorption is similar for all of the Examples 1–4, indicating that the silica is deposited substantially exclusively at the crystal exterior. Finally, the triply-treated catalyst exhibits diffusivity about sixty-five times lower than that of the untreated material. This observation corresponds, in a general way, with the estimated quantity of silica added to the catalyst, indicating that silica deposition has introduced a substantial diffusion barrier.

EXAMPLE 5

Catalytic evaluation of selectivated catalyst was conducted in an automated unit with on-line sampling. One gram of the triply-coated material (Example 4) was loaded into a 0.25 inch diameter stainless steel tube reactor. The sample was heated to 538° C. in 200 cc/min. air at a heating rate of 2.0° C./min. Pure toluene was then introduced at 485° C., 4 WHSV, 2 $H_2$/HC and 500 psig. After 20 hours on stream the catalyst exhibited 80% p-xylene at 37% conversion. Varying the WHSV showed that very high p-xylene selectivities were possible, e.g., 96% p-xylene at 19% conversion with a WHSV of 16.

To determine the activity/selectivity of the selectivated catalyst, reactor temperature was varied to obtain a profile of toluene conversion as a function of temperature. For example, at 465° C., 4 WHSV 2 $H_2$/HC and 500 psig, the catalyst exhibited 93% p-xylene at 29% conversion.

EXAMPLE 6

To determine the level of permanency of the selectivation, the used catalyst of Example 5 was air-calcined. After 24 hours on stream, at 466° C., 4 WHSV, 2 $H_2$/HC and 500 psig on pure toluene feed, the catalyst profile had changed to 93% p-xylene at 30% conversion. Thus, excellent catalyst performance was maintained after the regeneration.

EXAMPLE 7

In order to further examine the properties of the modified catalyst of Example 5, in situ trim-selectivation with 0.1 wt. % dimethylphenylmethyl polysiloxane (Dow-550) in toluene was initiated for a four hour period (485° C., 4 WHSV, 2$H_2$/HC and 500 psig). This trimming resulted in an increase in para-xylene selectivity, i.e., 91% para-xylene at 32% conversion versus 86% para-xylene at 35% conversion. Continued trimming under the same reaction conditions resulted in very high para-xylene selectivities.

EXAMPLE 8

HZSM-5/$SiO_2$ with a crystal size of approximately 1.6 microns was subjected to four consecutive treatments with dimethylphenylmethyl polysiloxane (Dow-550) as described above and illustrated by Examples 2–4. A sample of this modified material weighing one gram was loaded into a 0.25 inch diameter, stainless steel tube reactor. The sample was pre-dried at 300° C. for several hours. Then a selective toluene disproportionation reaction run was initiated using a pure toluene feed at 484° C., 4 WHSV, 2 $H_2$/HC and 500 psig. The results are shown below in Table 2.

EXAMPLE 9

Several grams of the multiply-coated catalyst described in Example 8 was steamed (100% steam) for four hours at 204° C., at 1 atmosphere. Then the activity and selectivity of the steamed catalyst were evaluated by performing a STDP run as described in Example 8. The results are shown in Table 2.

EXAMPLE 10

Several grams of the multiply-coated catalyst described in Example 8 was steamed (100% steam) for four hours at 316° C., at 1 atmosphere. Then the activity and selectivity of the steamed catalyst were evaluated by performing a STDP run as described in Example 8. The results are shown in Table 2.

EXAMPLE 11

Several grams of the multiply-coated catalyst described in Example 8 was steamed (100% steam) for four hours at 371° C., at 1 atmosphere. Then the activity and selectivity of the steamed catalyst were evaluated by performing a STDP run as described in Example 8. The results are shown in Table 2.

EXAMPLE 12

Several grams of the multiply-coated catalyst described in Example 8 was steamed (100% steam) for four hours at 500° C., at 1 atmosphere. Then the activity and selectivity of the steamed catalyst were evaluated by performing a STDP run as described in Example 8.

Table 2, below, provides data comparing activity and selectivity values for the unsteamed (Example 8) and variously steamed (Examples 9–12) multiply-coated catalysts.

TABLE 2

| Example | Catalyst | Para-selectivity at 25% toluene conversion | WHSV needed to achieve 25% toluene conversion |
|---|---|---|---|
| 8 | Unsteamed | 86 | 4 |
| 9 | Steamed at 204° C. | 92 | 9 |
| 10 | Steamed at 316° C. | 96 | 10 |
| 11 | Steamed at 371° C. | 87 | 3.5 |
| 12 | Steamed at 500° C. | 83 | 2 |

Catalyst samples steamed for four hours at 204° C. (Ex. 9) or 316° C. (Ex. 10) were both more active and more selective than unsteamed material, while higher temperature steaming (e.g., 500° C., 4 hours) resulted in significant loss in activity and a decrease in selectivity (Ex. 12). Material steamed at 371° C. (Ex. 11) exhibited activity and selectivity commensurate with the unsteamed material (Ex. 8).

Importantly, the mildly steamed materials, Ex. 9 (204° C.) and Ex. 10 (316° C.) give 25% conversion at 9 and 10 WHSV, respectively, while the unsteamed material, Ex. 8, requires 4 WHSV. Thus, low temperature steaming gave a 2–3 fold increase in activity. The material steamed at high temperature, Ex. 12, required 2 WHSV for this conversion level, and thus, was only half as active as the unsteamed material.

EXAMPLE 13

The catalyst of this Example was prepared via a multiple coating procedure. 5.38 gm of the untreated HZSM-5/$SiO_2$ material with a crystal size of 1.6 microns was subjected to three consecutive treatments with dimethylphenylmethyl polysiloxane (Dow-550) in dodecane. For each treatment ca. 1.9 gm of dimethylphenylmethyl polysiloxane (Dow-550) dissolved in 10 gm of dodecane served as the impregnation solution. After each treatment the catalyst was calcined in air at 5° C./min. to 538° C. and held for 0.5 hr. The total weight gain of the catalyst was approximately 8 wt. %.

The STDP runs were conducted in an automated unit with on-line sampling. Approximately one gram of catalyst extrudate was loaded into a 0.25 inch diameter, stainless steel tube reactor.

The catalytic run was initiated with pure toluene feed at 486° C., 4 WHSV, 2 $H_2$/HC and 500 psig. Initially the catalyst exhibited 89% p-xylene at 30% conversion (486° C., 4 WHSV, 2 $H_2$/HC and 500 psig). After 20 hours on stream, catalyst activity improved slightly to 92% p-xylene at 28% conversion. A WHSV scan at 486° C., 2 $H_2$/HC and 500 psig, showed that the catalyst produced very high p-xylene levels at lower conversion. At 8 WHSV, 96% p-xylene was obtained at 21% conversion. Thus, the change to a solvent of lower volatility appears not to have a detrimental effect on catalyst selectivity. A temperature scan at 4 WHSV, 2 $H_2$/HC and 500 psig, showed that high para-selectivity (>90%) could be obtained throughout the ca. 80° C. temperature range studied. For example, 95% p-xylene was obtained at 23% conversion at 465° C.

EXAMPLE 14

Following the catalytic run described in Example 13, the catalyst was removed from the catalytic unit. To confirm the degree of permanency of the selectivation, the catalyst was regenerated by calcining rapidly in air at 5° C./min. to 538° C. in a muffle furnace. After calcination, an initial sample, taken during a catalytic run at 486° C., 4 WHSV, 2 $H_2$/HC and 500 psig on pure toluene feed, showed 86% p-xylene at 24% conversion. After several hours on stream catalyst selectivity improved to 90% p-xylene at about 22% conversion. The overall loss in activity of the regenerated catalyst (ca. 25%) compared to the starting modified catalyst may be attributable to possible inadvertent steaming resulting from the rapid air calcination of the regeneration.

EXAMPLE 15

To 20.0 grams of untreated HZSM-5/$SiO_2$ having a crystal size of 1.6 microns was added 3.88 grams of dimethylphenylmethyl polysiloxane (Dow-550) dissolved in 60 cc of hexane. The catalyst was agitated in the silicone solution for several minutes and the hexane was distilled off by high vacuum distillation. The dry catalyst was then calcined at 1° C./min. in nitrogen to 538° C. After allowing the sample to cool to room temperature, the sample was then calcined in air at 1° C./min. to 538° C. and held for 3 hours. The silica-modified catalyst had gained 1.4 wt. %, presumably as $SiO_2$. The catalyst was then treated in a similar manner an additional three times with 6.77 grams, 6.82 grams and 6.78 grams of Dow-550, respectively. The resulting additional weight gains were 3.54 wt. % 1.67 wt. % and 1.39 wt. %, respectively, for a total weight gain of about 8.23 wt. % after the four silicone treatments.

Catalytic activity and selectivity were assessed by performing an STDP run in an automated unit with on-line sampling. Approximately one gram of the modified catalyst was loaded into a 0.25 inch diameter, stainless steel tube reactor. The sample was heated to 538° C. in 200 cc/min. air at a rate of 2.0° C./min. The catalytic run was initiated with pure toluene feed at 445° C., 4 WHSV, 2 $H_2$/HC and 500 psig. A temperature scan showed that the catalyst was active and selective. For example, at 485° C., with other conditions identical, and at 22 hours on stream, the catalyst exhibited 88% p-xylene at 32% conversion at 465° C., with other conditions unchanged, the catalyst showed 88% p-xylene at 26% conversion, after seven hours on stream.

Upon calcination to regenerate the catalyst, the sample produced 91% p-xylene and 30% conversion at 485° C., 4 WHSV, 2 $H_2$/HC and 500 psig. Thus catalyst performance was maintained upon regeneration.

EXAMPLE 16

To assess the effect of catalyst bulk handling e.g., loading, unloading, etc., a sample of the extrudate of Example 15 was crushed to 14/30 mesh and tested for catalytic activity and selectivity. A one-gram sample was loaded and a catalytic run was performed as described in Example 15.

The catalytic run was initiated with pure toluene feed at 445° C., 4 WHSV, 2 $H_2$/HC and 500 psig. A temperature scan showed that the catalyst was active and selective. After 8 hours on stream the catalyst exhibited 76% p-xylene at 37% conversion (485° C., 4 WHSV, 2 $H_2$/HC and 500 psig). After 19 hours on stream the catalyst exhibited 85% p-xylene at 32% conversion (485° C., 6 WHSV, 2 $H_2$/HC and 500 psig).

Thus, after an equivalent amount of time on stream, the crushed extrudate showed approximately the same activity/selectivity profile as the original modified material. These results suggest that physical damage to ex situ selectivated catalyst extrudate results in only minor losses (i.e., 3%) in catalyst selectivity; however, some of this loss may be regained with time on stream.

To assess the permanency of the selectivation and the effect thereon of the crushing process, the catalyst was regenerated by air calcination as described in Example 15. The catalyst showed 87% p-xylene at 32% conversion (485° C., 6 WHSV, 2 $H_2$/HC and 500 psig), roughly equivalent to the selectivity and activity of the crushed catalyst prior to regeneration. Crushing has apparently no effect on the regeneration behavior of the multiply-silicone coated catalyst.

EXAMPLE 17

105.0 grams of untreated HZSM-5/$SiO_2$ (1/16 inch extrudate dried at 130° C.) with a crystal size of 0.2 micron, was added to a solution of 10.0 grams dimethylphenylmethyl polysiloxane (Dow 550) dissolved in 92 grams of dodecane. The catalyst was mixed with the silicone solution at room temperature for two hours. Then the excess solvent was removed by filtration followed by a two step calcination procedure. The extrudate was heated in $N_2$ to 140° C. and held for two hours then heated in $N_2$ at 2° C./min to 538° C. and held for two hours. The sample was then cooled in $N_2$ to 300° C. at which temperature air was introduced followed by heating at 2° C./min to 538° C. and held for four hours. After cooling in $N_2$ to room temperature, the catalyst was determined to have gained 5.7 wt. %.

111.0 grams of the once-treated catalyst was added to a solution of 10.0 grams dimethylphenylmethyl polysiloxane (Dow 550) dissolved in 92 grams of dodecane. The catalyst was mixed with the silicone solution at room temperature for two hours. Then the excess solvent was removed by filtration followed by a two step calcination procedure. The extrudate was heated in $N_2$ to 140° C. and held for two hours then heated in $N_2$ at 2° C./min to 538° C. and held for two hours. The sample was then cooled in $N_2$ to 300° at which temperature air was introduced followed by heating at 2° C./min to 538° and held for four hours.

98.0 grams of the twice-treated catalyst was added to a solution of 9.6 grams dimethylphenylmethyl polysiloxane (Dow 550) dissolved in 88 grams of dodecane. The catalyst was mixed with the silicone solution at room temperature for two hours. Then the excess solvent was removed by filtration followed by a two step calcination procedure. The extrudate was heated in $N_2$ to 140° C. and held for two hours then heated in $N_2$ at 2° C./min to 538° C. and held for two hours. The sample was then cooled in $N_2$ to 300° at which temperature air was introduced followed by heating at 2° C./min to 538° C. and held for four hours. After cooling in $N_2$ to room temperature, the catalyst was determined to have gained 2.0 wt. %.

96.0 grams of three times-treated catalyst was added to a solution of 9.4 grams dimethylphenylmethyl polysiloxane (Dow 550) dissolved in 86 grams of dodecane. The catalyst was mixed with the silicone solution at room temperature for two hours. Then the excess solvent was removed by filtration followed by a two step calcination procedure. The extrudate was heated in $N_2$ to 140° C. and held for two hours then heated in $N_2$ at 2° C./min to 538° C. and held for two hours. The sample was then cooled in $N_2$ to 300° C. at which temperature air was introduced followed by heating at 2° C./min to 538° and held for four hours. After cooling in $N_2$ to room temperature, the catalyst was determined to have gained 2.0 wt. %.

Two grams of the four times-treated catalyst was evaluated in an automated unit with on line sampling. The sample was loaded into a 0.305" stainless steel tube reactor and then heated in hydrogen at 3.5° C./min to 425° C. in 40 cc/min hydrogen. Pure toluene was introduced at 425° C. at 4 WHSV, 1.5-2 $H_2$/HC and 300 psig. Representative performance data are shown below in Table 3.

TABLE 3

| Conditions: 300 psig, 4 WHSV | | |
|---|---|---|
| Toluene Conversion (wt. %) | 30 | 30 |
| Para-Selectivity (wt. %) | 95 | 95 |
| Temperature (°C.) | 428 | 426 |
| $H_2$/HC | 2.0 | 1.5 |
| Product Yields (wt. %) | | |
| Para-Xylene | 12.4 | 12.3 |
| Total Xylenes | 13.0 | 13.0 |
| Benzene | 14.4 | 14.8 |
| Bz/Xyl (molar) | 1.51 | 1.55 |
| Ethylbenzene | 0.4 | 0.5 |
| $C_5-$ | 1.3 | 1.8 |
| $C_9+$ | 0.4 | 0.4 |

EXAMPLE 18

50.0 grams of untreated HZSM-5/$SiO_2$ (1/16 inch extrudate, dried at 105° C.) having a crystal size of 1.6 microns was added to a solution of 4.6 grams of dimethylphenylmethyl polysiloxane (Dow-550) dissolved in 49 grams of dodecane. The catalyst was allowed to contact/absorb the silicone solution for several minutes after which the dodecane was stripped under nitrogen at 210°-220° C. The catalyst was then placed in a metal box and calcined in a muffle furnace at 2° C./min. in a 80%/20% $N_2$/air mixture (60 cc/min. total) to 538° C. The catalyst was held at 538° C. for about 4 hours. After cooling under $N_2$ the silica modified catalyst was found to have gained 1.3 wt. %.

50.7 grams of the once-treated catalyst was added to a solution of 4.6 grams of dimethylphenylmethyl polysiloxane (Dow-550) dissolved in 50 grams of dodecane. The catalyst was allowed to contact/absorb the silicone solution for several minutes after which the dodecane was stripped under nitrogen at 210°-220° C. The catalyst was then placed in a metal box and calcined in a muffle furnace at 2° C./min. in a 80%/20% $N_2$/air mixture (60 cc/min. total) to 538° C. The catalyst was held at 538° C. for about 4 hours. After cooling under $N_2$ the silica modified catalyst was found to have gained 3.1 wt. %.

51.2 grams of the twice-treated catalyst was added to a solution of 2.4 grams of dimethylphenylmethyl polysiloxane (Dow-550) dissolved in 51 grams of dodecane. The catalyst was allowed to contact/absorb the silicone solution for several minutes after which the dodecane was stripped under nitrogen at 210°-220° C. The catalyst was then placed in a metal box and calcined in a muffle furnace at 2° C./min. in a 80%/20% $N_2$/air mixture (60 cc/min. total) to 538° C. The catalyst was held at 538° C. for about 4 hours. After cooling under $N_2$ the silica modified catalyst was found to have gained 2.1 wt. %.

The catalyst was divided into two 25 gm portions. One portion was steamed at 316° C. for four hours in 100% steam, and was tested using the toluene disproportionation reaction as described below. The results are compared with the performance of the unsteamed portion of the multiple selectivated catalyst as well as with a coke selectivated catalyst.

TABLE 4

| Conditions: 500 psig, 4 WHSV, 2 $H_2$/HC | | | |
|---|---|---|---|
| | Coke Selectivation | Ex-Situ Steamed | Ex-Situ Unsteamed |
| Toluene Conversion (wt. %) | 30 | 30 | 29 |
| Para-Selectivity (wt. %) | 93 | 93 | 89 |
| Average Temperature (°C.) | 464 | 471 | 474 |
| Product Yields (wt. %) | | | |
| Para-Xylene | 11.2 | 11.7 | 11.9 |
| Total Xylenes | 12.0 | 12.6 | 13.4 |
| Benzene | 14.8 | 14.4 | 12.7 |
| Bz/Xyl (molar) | 1.7 | 1.55 | 1.29 |
| Ethyl Benzene (EB) | 0.51 | 0.65 | 0.52 |
| EB/Total $C_8$ | 4.0 | 4.9 | 3.7 |
| $C_5-$ | 2.4 | 2.0 | 2.0 |
| $C_9+$ | 0.57 | 0.64 | 0.64 |

The performance of the ex situ selectivated catalyst is apparently similar to that of the coke selectivated catalyst. For example, the triple silicone treated catalyst showed only slightly lower activity, as indicated by the higher average temperature required (471° C. vs. 464° C.). The yields of the ex situ selectivated catalyst, however, were generally more favorable than those of the coke selectivated sample. For example, the p-xylene yield was fractionally higher for the ex situ catalyst than for the coke catalyst.

EXAMPLE 19

A comparison was made of the activity and selectivity of catalyst selectivated via a single silica coating and catalyst selectivated via the multiple coating technique in accordance with the present invention.

50.2 grams of untreated HZM-5/$SiO_2$ (1/16 inch extrudate, dried at 105° C.) having a crystal size of 1.6 microns was added to a solution of 11.6 grams of dimethylphenylmethyl polysiloxane (Dow-550) dissolved in 50 grams of dodecane. The catalyst was allowed to contact/absorb the silicone solution for several minutes after which the dodecane was stripped under nitrogen at 210°-220° C. The catalyst was then placed in a metal box and calcined in a muffle furnace at 2° C./minute in a 80%/20% N$_2$/air mixture (60 cc/min total) to 538° C. The catalyst was held at 538° C. for ca. 4 hours. After cooling under N$_2$ the silica modified catalyst was found to have gained 5.2 wt. %.

The performance of the once-selectivated catalyst was evaluated using the toluene disprorortionation reaction as described below. The results are compared with the performance of the three times-selectivated catalyst of Example 16. It is shown that, at the same toluene conversion level, the triply treated catalyst is much more selective than the singly treated catalyst.

TABLE 5

| Single v. Multiple Ex-Situ Treatments | | |
|---|---|---|
| | Single | Triple |
| Attempted Wt. % Silica | 13.2 | 13.2 |
| Actual Wt. % Silica | 5.2 | 6.5 |
| Reaction Conditions | | |
| Temperature, °C. | 445 | 465 |
| H$_2$/HC | 2 | 2 |
| Pressure (psig) | 500 | 500 |
| WHSV | 3 | 3 |
| Toluene Conversion (Wt. %) | 29 | 29 |
| Xylene Yields (Wt. %) | | |
| Xylenes | 15.1 | 12.3 |
| Para Xylene | 4.9 | 11.3 |
| Para-Selectivity | 32 | 92 |

EXAMPLE 20

The catalyst examined in this example was prepared via a multiple coating procedure. The untreated HZHM-5/SiO$_2$ material was subjected to two consecutive treatments with dimethyl-phenylmethyl polysiloxane (Dow-550), intended to add ca. 5 wt. % as silica. The detailed treatment is described below.

6.9 grams of untreated HZSM-5/SiO$_2$ with a crystal size of 1.6 microns (1/16 inch extrudate, dried at 300° C.) was added to a solution of 0.65 grams of dimethyl-phenylmethyl polysiloxane (Dow-550) dissolved in 3 grams of dodecane. The catalyst was then placed in a vertical tube furnace and calcined at 2° C./minute in an 80%/20% N$_2$/air mixture (60 cc/min total) to 538° C. The catalyst was held at 538° C. for ca. 3 hours. After cooling under N$_2$ the silica modified catalyst was found to have gained 2.9 wt. %.

7.1 grams of the modified catalyst was added to a solution of 0.66 grams of dimethylphenylmethyl polysiloxane (Dow-550) dissolved in 3 grams of dodecane. The catalyst was then placed in a vertical tube furnace and calcined at 2° C./minute in an 80%/20% N$_2$/air mixture (60 cc/min total) to 538° C. The catalyst was held at 538° for ca. 3 hours. After cooling under N$_2$ the silica modified catalyst was found to have gained 2.7 wt. %.

The performance of the twice modified catalyst was evaluated by performing a selective ethylbenzene disproportionation (SEBDP) run in an automated unit with on-line sampling. Approximately one gram of the modified catalyst was loaded into a 0.25 inch diameter, stainless steel tube reactor.

The catalytic run was initiated with ethylbenzene feed at 6 WHSV, 28 psig and 0 H$_2$/HC. Data were obtained over a 20 day period on stream at temperatures between about 314° C. and about 337° C. An aging rate of 0.6° C./day was observed after about 7 days. Over the entire run, p-diethylbenzene selectivity averaged about 97.4% at 13-14% ethylbenzene conversion.

EXAMPLE 21

The performance of the modified catalyst of Example 20 was further evaluated by performing a SEBDP run using a sample of the modified catalyst in the presence of hydrogen diluent co-feed.

The catalytic run was initiated with ethylbenzene feed at 10 WHSV, 85-100 psig and 1.0 H$_2$/HC. The activity and selectivity of the catalyst were monitored over a period of over 11 days at various temperatures.

After reaching an apparent state, the conversion of ethylbenzene remained at 20% for approximately 170 hours (1.0 H$_2$/HC, 350° C., 85 psig, 10 WHSV). In the absence of hydrogen co-feed under these conditions, a catalyst aging rate of about 4° C./day is expected. In sharp contrast, in the presence of hydrogen little or no aging was observed over the time period studied.

While the invention has been described with reference to specific embodiments, it will be apparent that numerous variations, modifications, and alternative embodiments of the invention are possible, and accordingly all such variations, modifications, and alternative embodiments are to be regarded as being within the spirit and scope of the present invention as claimed.

What is claimed is:

1. A process for enhanced shape selective disproportionation of ethylbenzene comprising:
   contacting a reaction stream comprising ethylbenzene, under disproportionation conditions, with a catalytic molecular sieve which has been modified by being exposed to at least two ex situ selectivation sequences, wherein the ex situ selectivation sequence includes the steps of contacting the catalytic molecular sieve with a silicon compound selected from the group consisting of silicones, silicone polymers, silanes, and alkoxysilanes in an organic carrier and subsequently calcining the catalytic molecular sieve.

2. The process of claim 1, wherein the disproportionation conditions comprise a temperature of from about 100° C. to about 760° C., a pressure of from about 0.1 atmosphere to about 200 atmospheres, and a weight hourly space velocity of from about 0.08 to about 2000.

3. The process of claim 1, wherein the catalytic molecular sieve has been modified by between two and six ex situ selectivation sequences.

4. The process of claim 1, wherein the catalytic molecular sieve has been modified by two ex situ selectivation sequences.

5. The process of claim 1, wherein the catalytic molecular sieve has been modified by three ex situ selectivation sequences.

6. The process of claim 1, wherein the silicone or silicone polymer is selected from the group consisting of

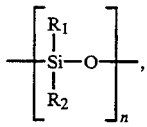

wherein R$_1$ and R$_2$ are independently selected from the group consisting of hydrogen, halogen, hydroxyl, alkyl, alkoxy, halogenated alkyl, aryl, halogenated aryl, aralkyl, halogenated aralkyl, alkaryl, and halogenated alkaryl, and n is between 2 and 1000; and the silane or alkoxysilane is selected from the group consisting of

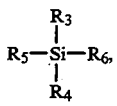

wherein $R_3$, $R_4$, $R_5$ and $R_6$ are independently selected from the group consisting of hydrogen, halogen, hydroxyl, alkyl, alkoxy, halogenated alkyl, aryl, halogenated aryl, aralkyl, halogenated aralkyl, alkaryl, and halogenated alkaryl.

7. The process of claim 1, wherein the silicon compound comprises dimethylphenylmethyl polysiloxane.

8. The process of claim 1, wherein the organic carrier is a linear, branched, or cyclic hydrocarbon.

9. The process of claim 1, wherein the organic carrier is a paraffin containing at least 7 carbon atoms.

10. The process of claim 1 wherein the organic carrier comprises heptane.

11. The process of claim 1 wherein the organic carrier comprises octane.

12. The process of claim 1 wherein the organic carrier comprises nonane.

13. The process of claim 1 wherein the organic carrier comprises decane.

14. The process of claim 1 wherein the organic carrier comprises undecane.

15. The process of claim 1, wherein the organic carrier component comprises dodecane.

16. The process of claim 1, wherein the organic carrier component comprises hydrocracker recycle oil.

17. The process of claim 1, wherein the catalytic molecular sieve comprises a zeolite having a Constraint Index from about 1 to about 12.

18. The process of claim 1, wherein the catalytic molecular sieve comprises ZSM-5.

19. The process of claim 18, wherein the catalytic molecular sieve comprises ZSM-5 having a crystal size larger than about 0.2 micron.

20. The process of claim 18, wherein the catalytic molecular sieve comprises ZSM-5 having a crystal size of about 0.2 micron or smaller.

21. The process of claim 1, wherein the catalytic molecular sieve contains an ion selected from the group consisting of hydrogen, hydrogen precursor, metals of Periodic Table Groups IB to VIII, organic cations, and combinations thereof.

22. The process of claim 1, wherein the catalytic molecular sieve is incorporated with binder before being modified.

23. The process of claim 22, wherein the binder is $SiO_2$.

24. The process of claim 1, wherein the catalytic molecular sieve is incorporated with binder after being modified.

25. The process of claim 24, wherein the binder is $SiO_2$.

26. The process of claim 1, wherein the catalytic molecular sieve is modified in an as-synthesized condition.

27. The process of claim 1, wherein the modified catalytic molecular sieve has been further modified by the step of steaming the modified catalytic molecular sieve under conditions comprising from about 1% to about 100% water vapor, a temperature of from about 100° C. to about 600° C., a pressure of from about 0.01 to about 50 psig, for a time of from about 0.1 to about 12 hours.

28. The process of claim 1, wherein the modified catalytic molecular sieve has been further modified by the step of in situ trim-selectivating the modified catalytic molecular sieve.

29. The process of claim 28, wherein the in situ trim-selectivating step comprises contacting the modified catalytic molecular sieve with a thermally decomposable organic compound selected from the group consisting of paraffins, cycloparaffins, olefins, cycloolefins, aromatics, alcohols, aldehydes, ethers, ketones, phenols, heterocyclics, and mixtures thereof at a temperature in excess of the decomposition temperature of the thermally decomposable organic compound.

30. The process of claim 29, wherein the organic compound is ethylbenzene.

31. The process of claim 28, wherein the in situ trim-selectivating step comprises contacting the modified catalytic molecular sieve with a reaction stream comprising toluene and a silicon compound selected from the group consisting of silicones, silicone polymers, silanes, and alkoxysilanes.

32. The process of claim 31, wherein the silicone or silicone polymer is selected from the group consisting of

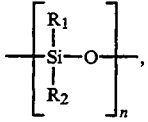

wherein $R_1$ and $R_2$ are independently selected from the group consisting of hydrogen, halogen, hydroxyl, alkyl, alkoxy, halogenated alkyl, aryl, halogenated aryl, aralkyl, halogenated aralkyl, alkaryl, and halogenated alkaryl, and n is between 2 and 1000; and the silane or alkoxysilane is selected from the group consisting of

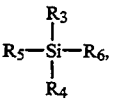

wherein $R_3$, $R_4$, $R_5$ and $R_6$ are independently selected from the group consisting of hydrogen, halogen, hydroxyl, alkyl, alkoxy, halogenated alkyl, aryl, halogenated aryl, aralkyl, halogenated aralkyl, alkaryl, and halogenated alkaryl.

33. The process of claim 31, wherein the silicon compound comprises dimethylphenylmethyl polysiloxane.

34. The process of claim 2, wherein the disproportionation conditions further comprise a hydrogen/hydrocarbon mole ratio of from greater than 0 to about 100.

* * * * *